US011389545B2

(12) United States Patent
Anderson (10) Patent No.: US 11,389,545 B2
(45) Date of Patent: Jul. 19, 2022

(54) BIOACTIVE NANOPARTICLES AND METHODS FOR MAKING SAME

(71) Applicant: AQUA REGENERATIVE THERAPIES LLC, San Diego, CA (US)

(72) Inventor: Sean Matthew Anderson, San Diego, CA (US)

( * ) Notice: Subject to any disclaimer, the term of this patent is extended or adjusted under 35 U.S.C. 154(b) by 340 days.

(21) Appl. No.: 16/244,084

(22) Filed: Jan. 9, 2019

(65) Prior Publication Data

US 2019/0209705 A1    Jul. 11, 2019

Related U.S. Application Data

(60) Provisional application No. 62/615,396, filed on Jan. 9, 2018.

(51) Int. Cl.

| A61K 47/69 | (2017.01) |
| C12Q 1/26 | (2006.01) |
| A61K 38/18 | (2006.01) |
| G01N 33/548 | (2006.01) |
| A61K 38/46 | (2006.01) |
| A61K 38/44 | (2006.01) |
| G01N 33/543 | (2006.01) |

(52) U.S. Cl.
CPC ...... *A61K 47/6939* (2017.08); *A61K 38/1841* (2013.01); *A61K 38/1866* (2013.01); *A61K 38/44* (2013.01); *A61K 38/443* (2013.01); *A61K 38/465* (2013.01); *A61K 47/6903* (2017.08); *C12Q 1/26* (2013.01); *C12Y 101/03004* (2013.01); *C12Y 104/03007* (2013.01); *C12Y 104/03011* (2013.01); *C12Y 301/01007* (2013.01); *G01N 33/548* (2013.01); *G01N 33/54346* (2013.01)

(58) Field of Classification Search
CPC .... C12Y 101/03004; C12Y 104/03007; C12Y 104/03011; C12Y 301/01007
See application file for complete search history.

(56) References Cited

U.S. PATENT DOCUMENTS

| 4,591,638 A * | 5/1986 | Ahrgren | A61P 3/06 |
| | | | 536/51 |
| 5,100,668 A * | 3/1992 | Edelman | A61K 9/167 |
| | | | 424/422 |
| 7,642,240 B2 * | 1/2010 | Cohen | A61K 47/61 |
| | | | 514/1.1 |
| 9,468,402 B2 * | 10/2016 | Petillo | A61B 5/14532 |
| 2005/0208476 A1 * | 9/2005 | Woltering | G01N 33/6863 |
| | | | 435/4 |
| 2009/0214513 A1 * | 8/2009 | Zhong | C12P 21/02 |
| | | | 514/1.1 |
| 2010/0203032 A1 * | 8/2010 | Barbier | A61P 43/00 |
| | | | 424/94.6 |
| 2012/0130320 A1 * | 5/2012 | Kassab | A61M 60/50 |
| | | | 604/256 |
| 2014/0349932 A1 * | 11/2014 | Whitehouse | A61K 38/1825 |
| | | | 514/9.1 |
| 2015/0159137 A1 * | 6/2015 | Sun | C12N 5/0667 |
| | | | 424/93.7 |
| 2016/0347869 A1 * | 12/2016 | Cowman | C08B 37/0072 |
| 2016/0348140 A1 * | 12/2016 | Cinti | C08B 37/0021 |

FOREIGN PATENT DOCUMENTS

| CN | 104399087 A | * | 3/2015 | |
| WO | WO-2017083659 A1 | * | 5/2017 | ........... A61K 9/0019 |
| WO | WO-2017159943 A1 | * | 9/2017 | ............ C07K 14/50 |

OTHER PUBLICATIONS

Roman et al. Polymers Advanced Tech. (2016; published online Feb. 2015) 27: 623-629 (Year: 2016).*
English translation of CN 104399087 A, published Mar. 2015, downloaded from the EPO on Feb. 27, 2021. (Year: 2015).*
Lim et al. Acta Biomteralia (2011) 7:986-995 (Year: 2011).*
Iakobsen et al. Macromolecular Chem. Phys. (Apr. 2017) vol. 218, 1600523, 9 pages (Year: 2017).*
Machine translation of WO-2017159943-A1 to Hong et al. (Year: 2017).*

* cited by examiner

*Primary Examiner* — Susan M Hanley
(74) *Attorney, Agent, or Firm* — Alpine IP (57) ABSTRACT

The present invention provides a composition of nanoparticles comprising a biological mimetic base component that forms the structure of the nanoparticle. By interacting with the functional groups of the base component, the half-life of a bioactive molecule is extended.

15 Claims, 5 Drawing Sheets

BIOACTIVE NANOPARTICLES AND METHODS FOR MAKING SAME

CROSS-REFERENCE TO RELATED APPLICATIONS

This Application claims the benefit of U.S. Provisional Patent Application No. 62/615,396, Titled Compositions and Methods For Stabilizing Bioactive Molecules, filed Jan. 9, 2018, which is hereby incorporated herein by reference in its entirety.

BACKGROUND OF THE INVENTION

1. The Field of the Invention

The present invention relates generally to the field of biotechnology. Specifically, the present invention relates to nanoparticle compositions that include a biological mimetic component that forms a nanoparticle and stabilizes a bioactive molecule.

2. Background of the Invention

Bioactive molecules present in medical therapies, diagnostics/devices, and mass-market consumables have limited shelf lives due to time dependent decreases in activity, which are described technically by the half-life of the molecule. The complex structures and hostile environments of bioactive molecules contributes to a fragile molecular conformation (tertiary and quaternary structure), which directly impacts the activity of the molecule. The stability of a bioactive molecule and the maintenance of active site integrity is related to molecular motion. The more the molecule moves or vibrates, or has the freedom to move or vibrate— higher temperatures, lower concentration—the less stable the molecule is. Stability increases when molecular motion is restricted or physically constrained.

Technologies that improve the stability of a bioactive molecule benefit several industries and aspects of life. Implantable sensors, systemic therapeutics, personal care items, alternative energy, and consumer electronics are a few examples of applications for bioactive stabilizing technology.

SUMMARY

The present invention relates to biotechnology and methods for stabilizing bioactive molecules through interaction with nanoparticles. The nanoparticles are composed of a synthetic biological mimetic base component that forms the structure of the nanoparticle and mimics a macromolecule of an animal extracellular matrix. The nanoparticles can be used on their own or with bioactive molecules. By interacting with the functional groups of the base component, the half-life of a bioactive molecule is extended (e.g., by at least 3-fold). The applications range from consumer goods to therapeutics that are applied to mammals through various delivery methods, including intravenous, subcutaneous, intramuscular, inhalation, oral, nasal, ocular, rectal, vaginal, or topical.

In one embodiment, the compositions include nanoparticles fabricated during an inverse emulsion polymerization reaction. The starting materials are biological mimetic hydrophilic subunits of either natural or preferably synthetic origin, and may include sulfate groups. Alternatively, or in addition, the starting material may also contain carboxylate groups, acrylate groups, vinyl groups, azido benzoyl groups, and other functional groups that can facilitate polymerization and/or initiate externally activated covalent conjugation. The starting material may also contain extracellular matrix and/or bioactive molecules and/or fragments thereof. These groups may either be part of the starting material or may have been engineered into the starting material through linkage chemistry such as EDC/NHS chemistry or similar procedure, and/or may be incorporated during the polymerization process. The polymerization reaction can form from a radical chain reaction, atom transfer radical polymerization, and/or from linkage between two complementary functional groups such as Michael addition or Click chemistry. The inverse emulsion is characterized by reverse micelles stably dispersed in an oil-based continuous phase (i.e., a water in oil emulsion). The reverse micelles include an emulsifier and an aqueous component (i.e, water) and one or more hydrophilic components such as starting monomers, polymers, and/or reaction components. The molecular weight of the emulsifier may be selected to facilitate stable reverse micelle formation. For example, non-ionic emulsifiers such as polysorbates and sorbitans have been found to be effective for achieving stable reverse micelle formation of the hydrophilic components.

The nanoparticles are formed from polymerization of the reaction components in the template of the reverse micelles. In one embodiment, the reverse micelles create nanoparticles with a median particle size less than 800 nm, preferably less than 500 nm or 250 nm or 100 nm. Reverse micelle nanoparticles can be formed by properly selecting and mixing the oil component, emulsifier, and aqueous component. In some embodiments, stable reverse micelles are formed using sonication. The oil component is typically a volatile substance such as hexane, which will house the inverse emulsion and allow the polymerization and other reactions to occur in the template of the reverse micelle. After the reaction is complete, the nanoparticle material is extracted from the inverse emulsion and purified by dialysis or ultrafiltration/diafiltration or equivalent method.

In certain embodiments, the invention provides a composition of nanoparticles that include un-sulfated and sulfated hyaluronic acid with a bioactive molecule, or a fragment thereof. The bioactive molecule may or may not be covalently bound to the nanoparticle.

In various embodiments, the bioactive material can be a growth factor or an extracellular matrix protein. Illustrative growth factors include epidermal growth factor, keratinocyte growth factor, nerve growth factor, vascular endothelial growth factor, and transforming growth factor. Illustrative extracellular matrix proteins include collagen, fibronectin, vitronectin, laminin, and fragments thereof.

In various embodiments, the material conjugated to the nanoparticle is derived from cell culture media or extracted from a culture of cells. Illustrative cell cultured media include cell conditioned media from a hypoxic culture of human fibroblast cells. Illustrative extracts from a culture of cells include human stem cell extracts, mesenchymal stem cell extracts, and stem cells "activated" using various means with the intent of collecting secreted growth factor products.

In various embodiments, the bioactive molecule is bound to the nanoparticle in densities ranging from zero bioactive molecules per nanoparticle to millions of bioactive molecules per nanoparticle. In some embodiments, the density of the bioactive molecule may be at least 0.1, 5, 10, 50 µg of bioactive molecule per mg. Nanoparticles containing different densities of bioactive molecules can be combined into different formulations. Nanoparticles containing different types of bioactive molecules can be combined into different formulations.

In various embodiments, the nanoparticles have an average characteristic dimension that is less than 500, 200, or 100 nm and/or greater than 5, 10, 20, or 50 nm, or within a range thereof. In illustrative embodiments, the nanoparticles have an average diameter that is in the range of approximately 10 nm to 220 nm, e.g., in the range of approximately 50 nm to 70 nm.

In certain embodiments, at least some nanoparticles in the composition are encapsulated in a degradable shell. In specific embodiments, the degradable shell is susceptible to degradation by a protease, such as a matrix metalloproteinase. In particular embodiments, the degradable shell includes a polyalkylene glycol, a carbohydrate, a peptide, or a combination thereof.

In certain embodiments, the nanoparticles contain an internal payload, such as drugs or DNA/RNA. In specific embodiments, the internal payload is a hydrophobic drug and forms a particle core with a nanoparticle monomer or polymer component. In particular embodiments, the internal payload is DNA or RNA and is stabilized in the particle core with monovalent and/or multivalent metal cations. In specific embodiments, the internal payload is a hydrophilic molecule, such as a peptide, that is encapsulated during the polymerization process.

In particular embodiments, the nanoparticles are present in a gel, such as a fibrin gel. In some embodiments, the gel additionally includes a soluble bioactive molecule or a fragment thereof, which can be the same as, or different from, the bioactive molecule bound to the nanoparticle. The soluble bioactive molecule can be, for example, a growth factor or an extracellular matrix protein. Illustrative growth factors include epidermal growth factor, keratinocyte growth factor, nerve growth factor, vascular endothelial growth factor, and transforming growth factor. Illustrative extracellular matrix proteins include collagen, fibronectin, vitronectin, laminin, and fragments thereof.

In specific embodiments, the invention provides methods useful in promoting cell growth in tissue culture. Such method entails, in certain embodiments, a method of supplementing cell culture media with nanoparticle compositions, wherein the effective amount is sufficient to induce cell growth at a higher rate than in the absence of said composition.

In specific embodiments, where the bioactive molecule is an angiogenic growth factor, the invention provides methods useful in promoting various aspects of angiogenesis. Such method entails, in certain embodiments, a method of enhancing vascularization of ischemic regions of the brain, wherein the method includes administering an effective amount of any of the nanoparticle compositions described herein to an ischemic region of the brain, wherein the effective amount is sufficient to induce vascularization at a higher level than in the absence of said composition. The ischemic region of the brain can be present in a mouse or higher order organism. In illustrative embodiments, the composition is administered to a damaged or diseased site and or at the site of an implant.

In specific embodiments, the growth factor nanoparticle conjugates can be delivered transdermally. This route of administration includes application with a topical emulsion, microneedles, iontophoresis, electrophoresis, or laser ablation. In specific embodiments, the nanoparticle compositions described herein can be delivered through the stratum corneum using a topical emulsion containing reverse micelles in a hydrocarbon-based continuous phase of non-volatile organics such as vegetable oils or petroleum or mineral oil or plant oils. In specific embodiments, the nanoparticle compositions described herein can be delivered to the dermal layer by electroporation with an approved medical device. In illustrative embodiments, the composition of transforming growth factor conjugated to the nanoparticle is delivered through porcine skin with electroporation.

The stabilization of the foregoing growth factors using the nanoparticles of the present invention enhances the activity of these bioactive molecules in animals and is beneficial for regenerative medicine applications.

In specific embodiments, the invention provides methods useful in stabilizing enzymes in sensors, consumer electronics, and sequencing devices. The nanoparticle enzyme conjugates are deposited on a biosensor device, typically in a film coating of the biosensor device. In illustrative embodiments, the enzymes are glucose oxidase, glutamate oxidase, and acetylcholinesterase. Often, the ability of the sensors to work is limited by the stability of the enzyme. By stabilizing the bioactive molecules in implantable sensors, the useable life of the sensor will be extended.

In various embodiments, the nanoparticle compositions are lyophilized and suspended as an aerosol for inhalation and delivery through mammalian lungs.

In various embodiments, the nanoparticle compositions are formulated with the same pH and ionic strength of physiological fluid for direct injection into the circulatory system or intramuscular or subcutaneous and/or nasal and ocular regions of mammals.

In various embodiments, the nanoparticle compositions are formulated into a tablet or suppository for delivery through oral, rectal, or vaginal routes of administration.

In certain embodiments, the invention provides methods useful in separation and concentration of bioactive molecules.

In certain embodiments, the invention provides methods useful in stabilizing cell surface antigens or fragments thereof, in cancer immunotherapy applications.

In certain embodiments, the invention provides methods useful in stabilizing bioactive molecules during lyophilization.

In certain embodiments, the nanoparticle composition may be a personal care composition. By stabilizing the bioactive molecules in personal care formulations, the effectiveness of the products is enhanced.

BRIEF DESCRIPTION OF THE DRAWINGS

To further clarify the above and other advantages and features of the present invention, a more particular description of the invention will be rendered by reference to specific embodiments thereof which are illustrated in the appended drawings. It is appreciated that these drawings depict only illustrated embodiments of the invention and is therefore not to be considered limiting of its scope. The invention will be described and explained with additional specificity and detail through the use of the accompanying drawings in which.

DETAILED DESCRIPTION

I. Introduction

The nanoparticle compositions of the present invention include all or a portion of the following components: a base component which is functionalized with an internal crosslinking component, an external binding component, and an external crosslinking component, interacting with a bioactive molecule component, internal payload components and/ or shell components, which include a degradable component and an outer shell crosslinking component. In a preferred embodiment, the base component mimics a macromolecule (e.g., a carbohydrate macromolecule) of the extracellular matrix of an animal (e.g., heparan sulfate).

The concentrations of the base component, internal crosslinking subcomponent, external binding subcomponent, external crosslinking subcomponent, and optional internal payload component are selected and mixed in combination with other components to form nanoparticles. The nanoparticles are then exposed to and linked to the bioactive molecule component. Optionally, the nanoparticle can be further processed with other internal payload components and shell-forming components.

In certain embodiments, the present invention relates to nanoparticles composed of a biological mimetic material that, through its natural functional groups and functional groups introduced to the base component through the subcomponents, is capable of binding and then conjugating to a bioactive molecule, such as a growth factor, or fragment thereof, and the interaction of such with cell surface receptors and/or extracellular matrix proteins. In particular embodiments, the present invention further relates to reducing the therapeutic dose required of bioactive molecules (e.g., growth factors) by conjugating and clustering them to the nanoparticles. In some embodiments, the invention relates to enhancing the cell signaling activity of bioactive molecules (e.g., growth factors) by conjugating and clustering them to the nanoparticles. In certain embodiments, the invention relates to bioactive molecule-nanoparticles (e.g., growth factor-nanoparticles) loaded with an internal payload and encased in a degradable shell, which are useful in tissue engineering and drug delivery applications.

II. Components Used to Manufacture the Nanoparticle Compositions

1. Base Component

The base component includes one or more hydrophilic compounds suitable for use as a starting material for further functionalization, such as a sugar. The base component may also be a collection of hydrophilic monomers. The base component may include hydrophobic regions for the purpose of forming a hydrophobic nanoparticle core that can create a reservoir of hydrophobic drugs for delivery. The base component preferably includes several carboxylic acids which provide a high negative charge to the polymer and serve as conjugation sites for further polymer functionalization. The base component preferably includes carbohydrates, complex carbohydrates, glucosamines, glycosamioglycans, and sulfated glycosaminoglycans. The base component may be of natural or synthetic origin.

The base component possesses biological mimetic properties that, through its natural functional groups and functional groups introduced into the base component through the below subcomponents, will orient and bind a bioactive molecule into a physiologically significant conformation that stabilizes the bioactive molecule and extends its active half-life by at least 3-fold.

The base component forms the structure of the nanoparticle via interaction of subcomponents.

Suitable compounds that can be used in the base component include, but are not limited to: glucose, chitin, alginate, cellulose, hyaluronic acid, sucrose, trehalose, and sucralose.

In a preferred embodiment, the base component includes a glucosamine, a glycosaminoglycan, sulfated glycosaminoglycan, or a combination of these. Examples of preferred glucosamine compounds include N-acetylglucosamine, and other monomers of hyaluronic acid and heparin. Preferred glycosaminoglycans include hyaluronic acid, chitin, and alginate. Preferred sulfated glycosaminoglycans include heparin, heparin sulfate, and dextran sulfate.

Although not required, it is preferable for the base component alone or in combination with the external binding component to have non-animal origin (i.e., synthetic composition) to avoid undesired side effects from animal material. Although the mimetics may have similar properties to natural occurring macromolecules, the synthetic manufacturing process can produce subtle differences. For instance, naturally occurring heparan sulfate will have a structured distribution of sulfate groups whereas the mimetic can have a more random pattern of sulfate groups that creates functional differences, such as a lack of anti-coagulation properties. For purposes of this invention "synthetic" means a non-animal source.

2. Internal Crosslinking Subcomponent

Nanoparticle compositions contain chemical elements which internally bind individual monomers and/or polymer chains together. These internal crosslinking components can be engineered into the base polymer or can be introduced during the inverse emulsion polymerization reaction and simultaneously bind together different regions of the base material. For example, the base polymer can be modified by reacting an amine-containing internal crosslinking subcomponent with a carboxylic acid of the base polymer using EDC/NHS mediated linkage chemistry. During the inverse emulsion polymerization reaction, the internal crosslinking subcomponent can be activated and bind the polymer chains together into a nanoparticle formed in the template of the reverse micelle. The internal crosslinking subcomponent may have the same functional groups on the ends of the molecule, and the internal crosslinking subcomponent may be branched. The internal crosslinking subcomponent preferably includes two different functional groups on each side of a linear molecule. The internal crosslinking subcomponent preferably includes an amine group on one end and a vinyl or acrylate group on the other end. These internal crosslinking subcomponents have a carbon chain length greater than or equal to 0, 1, or 2, and less than or equal to 100, 50, or 20.

Suitable compounds that can be used as the internal crosslinking subcomponent in the present invention include, but are not limited to: amine-vinyl, amine-acrylate, vinyl-hydrazide, and acrylate-hydrazide.

The molecular weight of the internal crosslinking component is preferably less than 10 kDa, 5 kDa, or 2 kDa and/or greater than 10 Da, 250 Da, or 500 Da or in a range of any of the foregoing endpoints.

In a preferred embodiment, the internal crosslinking component includes aminopropyl methacrylamide (APMA).

3. External Binding Subcomponent

The base compositions include an external binding subcomponent. The external binding subcomponent attracts bioactive molecules including growth factors, extracellular matrix proteins, heparin binding factors, and enzymes or fragments thereof through a specific electrostatic interaction. The external binding subcomponent facilitates the binding of the bioactive molecule to the nanoparticles either directly or indirectly through an external crosslinking subcomponent. These external binding subcomponents can be engineered into the base polymer or can be introduced during the inverse emulsion polymerization reaction. For example, the base polymer can be modified by reacting an airline-containing external binding subcomponent with a carboxylic acid of the base polymer using DDC/NHS mediated linkage chemistry (1-ethyl-3-(3-dimethylaminopropyl) carbodiimide (EDC) in combination with N-hydroxysuccinimide (NHS)). The external binding subcomponent may be branched, but preferably includes a bioactive molecule binding functional group on one end and a base material binding functional group on the other end of a linear molecule. The external binding subcomponent preferably includes a sulfate group on one end and an amine group on the other end. These external binding subcomponents have a carbon chain length greater than or equal to 0, 1, or 2, and less than or equal to 100, 50, or 20, or within a range of any of the foregoing lengths.

Suitable compounds that can be used as the external binding subcomponent in the present invention include, but are not limited to: amine-sulfate, amine-ammonium, amine-phosphate, sulfate-hydrazide, ammonium-hydrazide, and phosphate-hydrazide.

The molecular weight of the external binding subcomponent is preferably less than 10 kDa, 5 kDa, or 2 kDa and/or greater than 10 Da, 250 Da, or 500 Da or in a range of any of the foregoing endpoints.

In a preferred embodiment, the external binding subcomponent includes aminoethyl hydrogen sulfate.

4. External Crosslinking Subcomponent

The compositions of the invention may include an external crosslinking subcomponent in cases where it is desirable to covalently bind and lock a bioactive molecule into a particular location/orientation on the nanoparticle. The external binding subcomponent can be used to electrostatically orient the bioactive molecule prior to activating the external crosslinking subcomponent. The external crosslinking subcomponent is typically an environmentally activated crosslinker. The environmental activation can be pH activated, temperature activated, light activated (e.g., UV light) or the like. These external crosslinking subcomponents can be engineered into the base polymer or can be introduced during the inverse emulsion polymerization reaction. For example, the base polymer can be modified by reacting an amine-containing external crosslinking subcomponent with a carboxylic acid of the base polymer using EDC/NHS mediated linkage chemistry. The external crosslinking subcomponent may be branched, but preferably includes an environmentally and/or externally activated covalent binding functional group on one end and a base material binding functional group on the other end of a linear molecule. The external covalent binding subcomponent preferably includes an azido benzoyl group on one end and a hydrazide group on the other end. These external covalent binding subcomponents have a carbon chain length greater than or equal to 0, 1, or 2, and less than or equal to 100, 50, or 20.

Suitable compounds that can be used as the external covalent binding subcomponent in the present invention include, but are not limited to: azido benzoyl hydrazide.

The molecular weight of the external covalent binding subcomponent is preferably less than 10 kDa, 5 kDa, or 2 kDa and/or greater than 10 Da, 250 Da, or 500 Da or in a range of any of the foregoing endpoints.

In a preferred embodiment, the external covalent binding subcomponent includes azido benzoyl hydrazide.

5. Bioactive Molecule Component

The composition may further include bioactive molecule components, which can bind to the nanoparticles electrostatically and/or covalently in a physiologically active conformation. These bioactive molecule components can be exposed to the nanoparticle compositions after the inverse emulsion radical polymerization that generates the nanoparticles and/or the extraction process that purifies the nanoparticles. The bioactive molecule components can be incubated with the particles, wherein they are attracted to the nanoparticle compositions through the external binding subcomponent. Once sufficient time has been allowed for the bioactive molecule components to interact with the nanoparticle compositions, the solution is exposed to an external and/or environmental factor that activates the external crosslinking subcomponent. The bioactive molecules may be growth factors of a single type or factors extracted from a cell culture. The bioactive molecule component preferably includes angiogenic growth factors. These growth factors are characterized by a dense region in the amino acid sequence of lysines and arginines which impart a region of positive charge in a molecule with a possible overall negative charge.

Suitable compounds that can be used as the bioactive component in the present invention include, but are not limited to: EGF, KGF, VEGF, TGF, NGF, factors from an activated stem cell culture, glucose oxidase, glutamate oxidase, acetylcholinesterase, choline oxidase, cell surface antigens in cancer immunotherapy, and enzymes in genetic sequencing technologies.

The molecular weight of the bioactive component is preferably less than 500 kDa, 250 kDa, or 100 kDa and/or greater than 100 Da, 250 Da, or 500 Da or in a range of any of the foregoing endpoints.

In a preferred embodiment, bioactive components include angiogenic growth factors, factors from stem cell culture, hypoxic cell culture, VEGF, TGF, glucose oxidase, glutamate oxidase, acetylcholinesterase, and choline oxidase.

6. Internal Payload Components

In certain embodiments, the nanoparticle compositions include an internal payload. The internal payload component can be hydrophilic or hydrophobic. If hydrophobic, the base component can contain hydrophobic regions for the purposes of binding the hydrophobic payload through van der waal forces. Examples of a hydrophobic payload include transition state inhibitor drugs and hormones. Preferably the internal payload is hydrophilic. Examples of hydrophilic payloads include peptides, protein, amino acids, DNA, and/or RNA. If the hydrophilic payload is DNA and/or RNA, the internal payload can be stabilized by monovalent and/or multivalent metal cations, or by DNA/RNA binding moieties such as peptides or sugars. The internal payload can be incorporated during the inverse emulsion radical polymerization or after the nanoparticle is made in an adsorption process.

Suitable compounds that can be used as the internal payload component in the present invention include, but are not limited to: hydrophobic drugs, RNA, DNA, peptides, protein, amino acids, and lipids.

The molecular weight of the internal payload component is preferably less than 50 kDa, 10 kDa, or 2 kDa and/or greater than 10 Da, 250 Da, or 500 Da or in a range of any of the foregoing endpoints.

In a preferred embodiment, the internal payload component includes hydrophobic drugs, RNA, DNA, peptides, protein, amino acids, and lipids.

7. Degradable Shell Components

In one embodiment, the nanoparticle compositions are encapsulated in a degradable shell. The degradable shell components comprise a crosslinker and an external and/or environmentally-sensitive base material. The crosslinker contains functional groups on both ends that allow it to bind together regions of the external and/or environmentally-sensitive base material. Preferably, the crosslinker has the same function groups on both ends of a liner molecule. In certain embodiments, the external and/or environmentally sensitive base material is degradable by a protease. Preferably, the protease is a matrix metalloproteinase. An example of crosslinkers include diamines. An example of externally sensitive base materials include MMP degradable peptide sequences. Materials may serve the purpose of both the crosslinker and the degradable component. The degradable shell component is added after the nanoparticle compositions has been bound to the bioactive component. The shell can be formed by polymerization or some other chain reaction that forms the shell over the nanoparticle compositions. The crosslinker is greater than or equal to 0, 1, or 2 carbons in length or less than or equal to 100, 50, or 20 carbons in length. In certain embodiments, the base material is greater than or equal to 0, 1, or 2 amino acids long and less than or equal to 500, 100, or 50 amino acids long.

Suitable compounds that can be used as the degradable shell component in the present invention include, but are not limited to: acrylamide, MMP sensitive acrylamide co-polymer, bisacrylamide, MMP sensitive bisacrylamide co-polymer, and APMA.

The molecular weight of the degradable shell components is preferably less than 50 kDa, 10 kDa, or 2 kDa and/or greater than 10 Da, 250 Da, or 500 Da or in a range of any of the foregoing endpoints.

In a preferred embodiment, the degradable shell component includes APMA, acrylamide, and bisacrylamide.

III. Methods for Manufacturing Nanoparticle Compositions

Embodiments of the invention relate to making nanoparticle compositions composed of a biological mimetic base material that forms the structure of the nanoparticle with subcomponents that impart specific functionality to the nanoparticle composition including: internal crosslinking to form the nanoparticle, external binding to attract bioactive molecules, and external crosslinking to lock bioactive molecules to the nanoparticle base material. There are also other optional components including internal payload and degradable shell. One purpose of the nanoparticle compositions is to stabilize bioactive molecules, which enhances both the activity and half-life of the bioactive molecule. The nanoparticle compositions may be manufactured by first forming a precursor composition, comprising the base component and subcomponents, and then immersing the precursor composition in an inverse emulsion along with other materials that initiate a polymerization reaction, and finally purifying the nanoparticles from the emulsion.

The nanoparticle compositions are formed by selecting appropriate concentrations of a base component, an internal crosslinking subcomponent, an external binding subcomponent, an external crosslinking subcomponent, and other constituents such as an internal payload component and mixing the components together in an inverse emulsion to form nanoparticles. The inverse emulsion is used to form the nanoparticles but is typically not part of the nanoparticle composition. In some embodiments, the inverse emulsion contains an oil continuous phase in which the oil has a viscosity similar to or less than water. In preferred embodiments, the oil phase is hexane. In some embodiments, the inverse emulsion contains an emulsifier and the emulsifier concentrations are selected to exceed the critical micelle concentration. In particular embodiments, the emulsifiers are low molecular weight surfactants. In some embodiments, the polymerization reaction requires initiation, and initiation components are added to the inverse emulsion during the mixing of components. In particular embodiments, the polymerization is a radical polymerization requiring ammonium persulfate. In some embodiments, the polymerization reaction includes mixing with sufficient agitation to form reverse micelle nanoparticles of aqueous phase in the oil continuous phase. In particular embodiments, the mixture is homogenized with an ultrasonic adapter. In some embodiments, the nanoparticle solution is separated from the polymerization solution. In particular embodiments, the nanoparticles are separated by liquid-liquid extraction with a high salt solution and then purified by dialysis or column separation or equivalent separation technique. In some embodiments, the nanoparticle compositions are incubated with a bioactive component. In particular embodiments, the nanoparticle compositions are incubated with the bioactive component with activation of the external crosslinker and then purified. In some embodiments, the bioactive molecule-nanoparticle conjugates are incubated with shell forming components. In particular embodiments, the bioactive molecule-nanoparticle conjugates are coated in a degradable shell that is sensitive to matrix metalloproteinases. In some embodiments, final formulation is achieved by buffer exchange or freeze drying. In particular embodiments, the final nanoparticle composition undergoes buffer exchange into a physiologically compatible solution.

The base material may have a concentration of greater than or equal to 1%, 5%, 10% and/or less than or equal to 99%, 90%, 70 C %, or 50% or within a range of the foregoing. The internal crosslinking subcomponent may be included in a concentration of greater than or equal to 0.1%, 1%, 5%, 10%, and/or less than or equal to 99%, 90%, 70%, or 50%. The external binding subcomponent may be included in a concentration greater than or equal to 0.1%, 1%, 5%, or 10% and/or less than 99%, 90%, 70%, or 50% or within a range of any of the foregoing endpoints. The external crosslinking subcomponent may be included in a concentration of at least 0.1%, 1%, or 5%, or 10% and/or less than or equal to 99%, 90%, 70%, or 50%, or within a range of the foregoing. The base material is functionalized with the subcomponents. Although not required, the functionalizing can be carried out using a crosslinking reaction. The crosslinking reaction may use EDC. EDC may be included in a concentration of greater than or equal to 0.01%, 0.1%, 1% and/or less than or equal to 99%, 90%, 70%, or 50%, or within a range of the foregoing.

After purification through dialysis, UF/DF, TFF, or equivalent method, the precursor composition is then mixed with an oil continuous phase to form micelles. The oil continuous phase may have a concentration of greater than or equal to 1%, 5%, 10% and/or less than or equal to 99%, 90%, 70%, or 50% or within a range of the foregoing. The emulsifiers used to stabilize the inverse emulsion can be greater than the critical micelle concentration and may be greater than or equal to 0.1%, 1%, 5% and/or less than or equal to 99%, 90%, 70%, or 50% or within a range of the foregoing. The materials used to initiate the polymerization, if necessary, such as ammonium persulfate and TEMED, may have a concentration of greater than or equal to 0.01%, 0.1%, 1% and/or less than or equal to 99%, 90%, 70%, or 50% or within a range of the foregoing. The mixing is carried out for a sufficient time that the emulsification nears completion (i.e., the concentration of micelles is near a maximum). Typically, the majority of the aqueous solution will be emulsified. The amount of mixing typically depends on the volume of the mixture. The mixing time may be greater than or equal to 10 seconds, 30 seconds, 1 minute, or 5 minutes and less than 20 minutes, 10 minutes, or 5 minutes or within a range of the foregoing. Typically, smaller volumes (e.g., less than 1 liter) tend to require shorter periods of mixing time and larger batches (e.g., greater than 10 liters requires longer mixing times). For example, mixing time may be greater than 45 min, but sonication time is less than 5 min.

In one embodiment, the mixing includes sonication. Sonication has been found to be surprisingly effective at forming micelles that will form nanoparticles in the desired diameter range.

The nanoparticle compositions are separated from the polymerization reaction by a series of extractions between the oil continuous phase and an extraction solution. The extraction solution may have a salt concentration of greater than or equal to 1%, 5%, or 10% and/or less than or equal to 50%, 30%, or 20%, or within a range of the foregoing. The volume of the extraction container may be greater than or equal to 25 ml, 50 ml, 100 ml and/or less than 500 L, 200 L, or 100 L, or within a range of the forgoing. The extraction time may be selected in combination with the extent of extraction required for each serial step (i.e. Earlier extraction steps required longer extraction time) and may be for a period of greater than or equal to 1 hour, 3 hours, 5 hours, or 1 day. The extraction of the nanoparticle solution from the emulsion may also be carried out by use of specialized filters.

The nanoparticle compositions undergo final formulation for customary final use. In one embodiment, the composition is purified by dialysis or column chromatography or equivalent technique. The nanoparticle compositions are purified against DI water to prevent aggregation. Purification in saline solution can promote aggregation by providing charge stabilization of the nanoparticle compositions with counter ions present in a saline solution. Alternatively, by purifying in DI water, the salts from the extraction solution are diluted, and aggregation is prevented by the natural charge repulsion between the nanoparticles. For filtration of a high concentration of nanoparticles during purification, DI water as the solvent is preferred. Filtration in a salted solution promotes aggregation. The volume of the container may be greater than or equal to 25 ml, 50 ml, 100 ml and/or less than 500 L, 200 L, or 100 L, or within a range of the forgoing. In some embodiments, the composition is submerged in liquid nitrogen and dried in a lyophilizer. The amount of liquid nitrogen and volume of lyophilization may be greater than or equal to 25 ml, 50 ml, 100 ml and/or less than 500 L, 200 L, or 100 L, or within a range of the forgoing.

In some embodiments, the formation of the nanoparticles can be determined using a particle size analyzer and/or by measuring polydispersity. In one embodiment, the emulsion has a polydispersity index of less than 0.8, 0.7, 0.6 or 0.5. The particle size of the nanoparticle can be measured with TEM, SEM, or DLS and be less than 800 nm, 500 nm, 200, or 100 nm.

After the nanoparticles are made and formed, they are incubated with the bioactive molecule in a saline solution. The bioactive molecule may be included in a concentration of at least 0.1%, 1%, 5%, or 10% and/or less than or equal to 99%, 90%, 70%, or 50%, or within a range of the foregoing. Other components that make up the balance of the composition (e.g., internal payload components, degradable shell components, etc.) may be used in concentrations that cumulatively are greater than 0.1%, 1%, or 5% and/or less than or equal to 99%, 90%, 70%, or 50%, or within a range of the foregoing. Typically, the external crosslinker is activated after the nanoparticles have been incubated with the bioactive molecule, but before the shell formation or other purification step.

The bioactive molecule-nanoparticle conjugates and/or shelled components with and without an internal payload are purified by dialysis or column chromatography or equivalent technique. The volume of the purification container and/or column may be greater than or equal to 25 ml, 50 ml, 100 ml and/or less than 500 L, 200 L, or 100 L, or within a range of the forgoing. The purification time may be for a period of greater than or equal to 1 hour, 3 hours, 5 hours, or 1 day.

The nanoparticle compositions undergo final formulation for customary final use. In one embodiment, the composition is purified by dialysis or column chromatography or equivalent technique. The volume of the container may be greater than or equal to 25 ml, 50 ml, 100 ml and/or less than 500 L, 200 L, or 100 L, or within a range of the forgoing. In some embodiments, the composition is submerged in liquid nitrogen and dried in a lyophilizer. The amount of liquid nitrogen and volume of lyophilization may be greater than or equal to 25 ml, 50 ml, 100 ml and/or less than 500 L, 200 L, or 100 L, or within a range of the forgoing.

In some embodiments, the confirmation of the nanoparticles binding to the bioactive molecule can be determined using an ELISA or another equivalent detection technique with and without the use of antibodies. In one embodiment, the growth factor is conjugated to the nanoparticle at a density of greater than 0.1, 5, 10, 50 μg bioactive molecule per mg of nanoparticle and/or less than 200, 100, or 50 mg/mg or within a range of any of the foregoing densities. The detection of the bioactive molecule-nanoparticle can be measured using a plate reader, scanner, or other equivalent detection technique.

The base component and its subcomponents are selected in combination with the bioactive molecule to ensure a stabilizing interaction. The nanoparticle can bind the bioactive molecules with a dissociation constant of less than 10, 1, or 0.1 micromolar.

IV. Nanoparticle Compositions Use and Delivery

The nanoparticle composition can be formulated into a biocompatible solution or powder that can be delivered into a mammal through invasive or non-invasive routes of administration. The biocompatible solution or powder may be formulated into a cream, foam, paste, gel, aerosol, saline solution for injection, or of the like. The delivery system includes the nanoparticle compositions and excipients needed for effective transfer into the physiologic environment. The dispersed nanoparticles have a particle size sufficiently small to migrate through mucosal membranes and mammal tissue. Forming nano-sized sugar-like particles was found to have a surprisingly large impact on stability and signaling activity of growth factors and other bioactive molecules.

This is in contrast to traditional growth factor delivery, which either use no stabilizers or use inert stabilizers such as albumin, polyethylene glycol (PEG), or sugars without a specific electrostatic interaction. The lack of stabilizers results in growth factors with a short half-life, unable to sustain any physiologically meaningful activity. To compensate, formulators will increase the concentration of the growth factors, which is expensive and can be dangerous (Regranex). Using stabilizers like albumin, PEG, or inert sugars enhances the growth factor half-life but not sufficiently to impart the activity required for a meaningful, sustained, biological response. Therefore, high costs and high concentrations are still required. The compositions of the present invention overcome these deficiencies using a nanoparticle technology that binds and locks growth factors, enhancing stability and activity.

The sugar-like nanoparticles described in this invention enhance stability by covalently binding labile growth factors to a structural support. The support system restricts molecular movement, which directly increases stability. The support also protects the growth factors from enzymatic and physical degradation, similar to the purpose of PEGylation. The nanoparticles enhance activity by clustering growth factors into nano-domains and orienting the growth factors in a physiologically relevant conformation due to the specificity of the interaction between the growth factor and the biological mimetic binding partner engineered into the nanoparticle composition. When the clustered growth factor complexes are presented to cell surface receptors, the activation of the intracellular signaling cascades increases. By using less growth factors for more signaling, the cost of the therapies and concentration required are reduced.

To achieve stability and enhanced activity, the mean particle size may be less than 800 nm, 500 nm, 300 nm, or 150 nm and/or greater than 10 nm, 20 nm, 50 nm, 100 nm, 150 nm or in a range of any of the foregoing upper and lower particle sizes. (50-70 nm)

The internal crosslinking subcomponent and its concentration are selected to form nanoparticles of the base component in the template of the reverse micelles formed during the inverse emulsion. The internal binding subcomponent may be of a single type or a plurality of types and may or may not require initiators and co-factors for polymerization.

The base component, external binding subcomponent, and external crosslinking subcomponent and their concentrations are chosen to attract, bind, and link the bioactive molecule component to the nanoparticle. Sugars and sugar-like polymer mimics are generally electronegative (base component). The negative charge of the nanoparticle attracts the positive charge of localized regions in bioactive molecules, which sometimes have an overall negative surface charge. This pocket of positive charge assists in orienting the growth factor correctly for presentation to the cell surface receptor. The external binding subcomponent typically contains sulfate, which is known to attract the heparin-binding domain of growth factors, and engage the bioactive molecule in a stable, specific electrostatic interaction. The external crosslinking subcomponent covalently locks the growth factor after the binding event. The external crosslinking subcomponent is activated by some kind of change in the environment, like temperature, pH, ionic strength, or introduction of some kind, like magnetism, light, or UV.

The nanoparticles themselves can be used as an additive to cell culture, to prolong the active life-span of the growth factors in the culture and increase the activity of the growth factors. The particles can also be used to separate bioactive molecules from a complex mixture, similar to a heparin column, complete with elution, if necessary. In these cases, the nanoparticles would be delivered via bolus delivery or lyophilized and packaged into a cassette or column.

The main use of the nanoparticles is to increase the stability of its bioactive binding partners and reduce the effective dose of bioactive binding partner required for therapeutic benefit. The bioactive molecule component and their concentrations are selected to provide instruction to resident cells (stem cells included) to repair, restructure, regenerate, and/or form novel biological structures that benefit mammals suffering from disease, including aging. The bioactive component may be of a single type or a plurality of types and may be produced recombinantly or collected from cell secretion due to stress.

The nanoparticles can also be used to deliver an internal payload to a cell via ligand-receptor binding and internalization of the particle. The internal payload and its concentration are selected to exert a therapeutic effect on a target (ie. transition-state inhibitor to enzyme in a cellular pathway, DNA to nucleus, RNA to cytoplasm, etc). The internal payload may be one type of drug or several types of drugs. The nanoparticle may be introduced as a pro-drug with a degradable shell around it. The shell serves the purpose of protecting the ligands until there is environmentally demanded activation of the delivery vehicle. When the shell degrades and presents the ligands, the internal payload becomes active. The shell components and their concentrations are selected to protect the nanoparticle in a certain, targeted environment (i.e. certain MMP expression, high/low pressure, etc.). The degradable shell components may be of a single type or many types.

The forgoing iterations of the nanoparticle compositions can be specifically designed to provide therapeutic benefit to a number of pathologies. Accelerated wound healing of ulcers, traumatic injuries, and surgical and cosmetic incisions is possible with this technology. The nanoparticle compositions are delivered to the wound healing environment through topical application of a cream, foam, gel (including liquid that transitions into a solid or semi-solid state due to enzymatic action or body temperature), or of the like. The delivery can be assisted into the subdermal layers with the aid of a device such as electroporation, iontophoresis, negative pressure, or any such mechanism that drives the nanoparticle compositions into the wound.

Regeneration of nerves from disease states that cause neuropathy is possible with this technology. This includes, but is not limited to diabetes, trauma, Alzheimer's, stroke, and general nerve/brain atrophy from aging. The nanoparticle compositions are delivered to the neuropathic environment through injection (cranial, intramusclar, subcutaneous, ocular, ear, etc), inhalation (nose, lung), oral, rectal, and vaginal. The nanoparticle compositions can be formulated into a physiologically stable saline solution for injection or ocular/nasal delivery. The nanoparticle compositions can be crystallized or lyophilized and provided with suitable excipients for inhalation. The nanoparticle compositions can be formulated into a suppository or cream for rectal and vaginal delivery.

Other examples of techniques for delivering nanoparticles are described in PCT application number PCT/US2012/039459, filed May 24, 2012, which is hereby incorporated herein by reference in its entirety.

The nanoparticle composition can be incorporated into a brain repair kit and used to regenerate brain tissue after stoke. A mixture of 99% nanoparticles without bioactive molecule and 1% nanoparticles with bioactive molecule, wherein the nanoparticles with bioactive molecule contain a weight ratio of 20:1 bioactive molecule to nanoparticle, can regrow brain tissue. PCT application number PCT/US2018/025554, filed Mar. 30, 2018, is hereby incorporated herein by reference in its entirety.

The nanoparticle composition can be incorporated into a hydrogel composition for use in regenerative medicine applications. Examples of methods for making hydrogels suitable for incorporation of the nanoparticle compositions of the present invention are described in PCT application number PCT/US2015/040962, filed Jul. 17, 2015, which is hereby incorporated herein by reference in its entirety.

The nanoparticle composition can be incorporated into a transdermal delivery composition, which can be used to reach the epidermis (topical) or dermal layers of the skin (with aid of electroporation device). The bioactive nanoparticle compositions of the invention can be used in combination with one or more of the compositions described in Applicant's U.S. Pat. No. 10,034,834 issued Jul. 31, 2018, which is hereby incorporated herein by reference in its entirety.

The bioactive nanoparticle compositions described herein can be incorporated into a biosensor. The biosensor may include a support (i.e., a physical component) with an optically or electrically active surface. Changes in the optical or electrically active surface are typically amplified and/or processed using circuitry.

The nanoparticle compositions can be applied as a coating or incorporated into a coating material that is applied to the electrically sensitive surface or active surface of the biosensor's physical component. The coating can include a polymeric material. The nanoparticle compositions can be incorporated into a coating using any technique known in the art so long as the coating and/or process is compatible with the nanoparticle composition (i.e., maintains adequate stability of the bioactive component). For example, the nanoparticle composition may be incorporated into the coating using a solvent, melting a polymer, or polymerizing a mixture of the nanoparticle composition and a polymerizable material. The coating can be applied using techniques such as spray coating, dip coating, spin coating and or the like. The biosensor may be an implantable device, including a biocompatible implant suitable for implantation into an animal and/or human. The biosensor may be a flexible, polymer-based neural probe. An example of a biosensor into which the nanoparticle compositions of the invention may be incorporated is described in U.S. Pat. No. 9,788,740, issued Oct. 17, 2017, which is hereby incorporated herein by reference in its entirety.

The nanoparticle compositions useful for biosensors can have stabilized, biologically active molecules that are useful for sensing reactions that occur in biological systems. In some embodiments, the biologically active molecule may be an enzyme. Examples of enzymes that can be used in the biosensors of the invention include signal binding proteins (e.g., neurotransmitter binding proteins such as acetylcholinesterase, which binds the neurotransmitter acetylcholine). Other examples of enzymes useful in the biosensors of the invention include oxidases such as glucose oxidase, glutamate oxidase, and choline oxidase. Those skilled in the art will recognize that the teachings of the invention can be used to stably incorporate other types of enzymes and/or biologically active molecules into biosensors.

In some embodiments, the nanoparticles are selected to stabilize the bioactive molecule in order to increase its half-life by at least 1.5, 2, or 3 times as compared to the biosensor with the enzyme incorporated without the nanoparticle.

One embodiment of the invention relates to a neural interface. The neural interface may be fabricated using all or a portion of the steps of depositing a bottom dielectric material on a substrate; etching openings in the bottom dielectric material for bottom electrodes; depositing and patterning bottom electrodes; depositing and patterning a bottom interconnection trace metal; depositing an interlayer dielectric material; depositing a stiffening shank material; depositing an interlayer dielectric material; patterning a stiffening shank from the stiffening shank material; depositing an interlayer dielectric material; depositing and patterning a top interconnection trace metal; depositing and patterning top electrodes; depositing a top dielectric material; etching openings in the top dielectric material for the top electrodes and connector openings; releasing the device from the substrate; and depositing the nanoparticle composition on an electrosensitive surface of the biosensor.

V. Examples

Example 1

The nanoparticles in Example 1 and Examples 2-5 were made by combining hyaluronic acid (base component) at a concentration of 10 mg/ml with aminopropyl methacrylamide (internal crosslinking subcomponent) at a concentration of 5 mg/ml, aminoethyl hydrogen sulfate (external binding subcomponent) at a concentration of 4 mg/ml, azidobenzoyl hydrazide (external crosslinking subcomponent) at a concentration of 5 mg/ml, and EDC at a concentration of 10 mg/ml. The solution was dissolved in DI water, mixed at room temperature for 2 hours, with pH maintained at 4.75.

The precursor solution was purified by spin columns with a MWCO of 3 kD. The buffer was exchanged into 100 mM acetic acid and concentrated to 100 mg/ml of the modified polymer.

The 100 mg/ml modified polymer in acetic acid solution was combined with hexane, span 80, tween 80, TED, and ammonium persulfate, and then exposed to sonication for 30 seconds, and then mixed overnight at room temperature in the dark to form the nanoparticles.

The nanoparticle solution was purified by liquid-liquid extraction using brine solution and hexane, then buffer exchanged into DI water using spin columns. The nanoparticle solution was filtered and stored in DI water until use. The nanoparticle solution was then diluted into saline solution for use.

The nanoparticles were combined with bioactive molecules, incubated overnight at 4 C with slow stirring, and then exposed to UV light for 10 min to activate the covalent crosslinker. The resultant solution was purified by spin column with a MWCO of 100 kD. The bioactive molecule-nanoparticle conjugates were then tested.

Figure 1A:
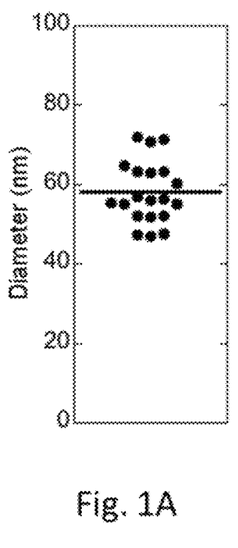
FIG. 1A shows the average diameter of nanoparticles made according to one embodiment of the invention.
Figure 1B:
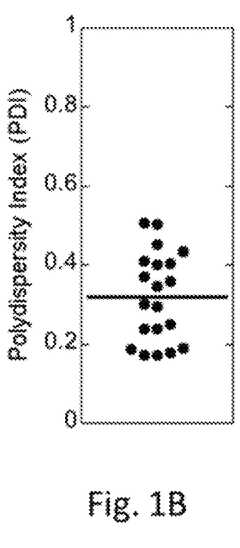
FIG. 1B shows the polydispersity index of the nanoparticles of FIG. 1A.

Dynamic light scattering data including Z-average particle diameters and polydispersity index were obtained with a Malvern Zetasizer (FIGS. 1A and 1B). FIGS. 1A and 1B show the diameter and polydispersity index of nanoparticles made according to one embodiment of the invention. Each data point in the diameter plot is the Z-average reading of a sample. The diameters for each Z-average reading range according to the polydispersity index, making it possible for nanoparticles greater than the range in the plot to exist in the system.

Example 2

Figure 2A:
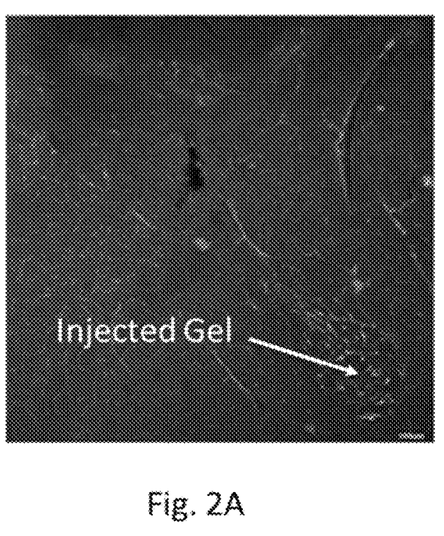
FIGS. 2A and 2B are images of mouse brain showing improved astrocyte migration from VEGF stabilized with nanoparticles according to one embodiment of the invention (FIG. 2B) as compared to VEGF delivered to mouse brain without the stabilizing nanoparticles.
Figure 2B:
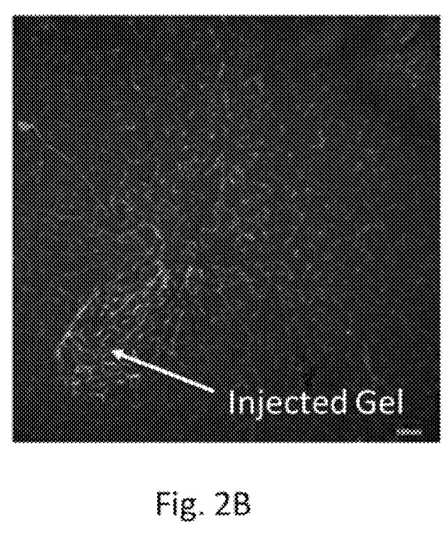

Micron sized gels with either soluble VEGF or nanoparticle bound VEGF at a concentration of 2 μg/ml were injected into a healthy mouse brain. After several days, the mice were sacrificed and the brains were examined for PECAM (vasculature) and GFAP (reactive astrocytes)—FIG. 2A is an image from mouse brain injected with soluble VEGF and FIG. 2B is an image of mouse brain with nanoparticle bound VEGF. In FIGS. 2A and 2B the vasculature appears red and the activated astrocytes are in green. The gel deposition sites show the strongest astrocyte activation as evidenced by the strong presence of green cells. However, the nanoparticle compositions promote migration of reactive astrocytes in the brain (the spreading of green from the injection gel), which according to recent reports in the literature (Anderson et al, Nature 2016), suggest the capacity for axon regeneration.

Example 3

Figure 3:
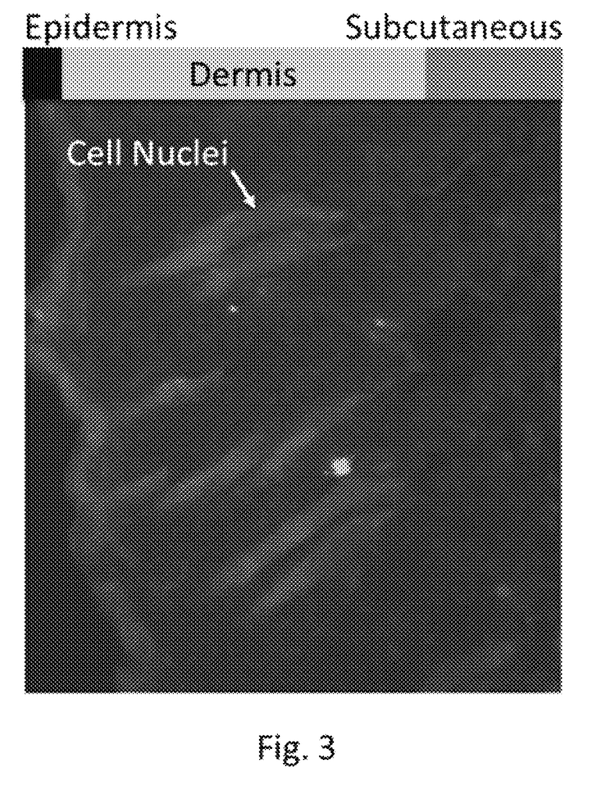
FIG. 3 is an image of porcine skin showing transdermal delivery of nanoparticle compositions through the porcine skin aided by an electroporation device.

A topical emulsion with nanoparticle-bound TGF-B3 growth factor was applied to cadaver porcine skin. After exposure to an electroporation device, the skin was examined for TGF-B3 transport via fluorescent labeling. The TGF-B3 appears to distribute into the dermal layer, but not the subcutaneous layer (FIG. 3).

Example 4

Figure 4A:
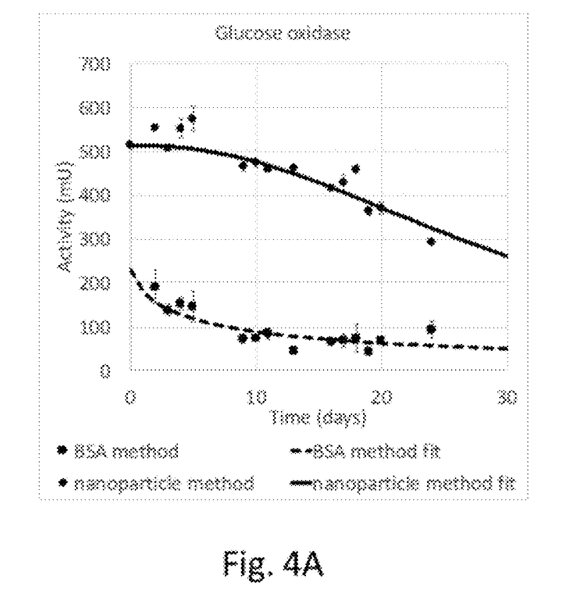
FIGS. 4A-4C show improvements to the half-life of enzymes stabilized in example nanoparticle compositions and used in biosensors according to embodiments of the invention.
Figure 4B:
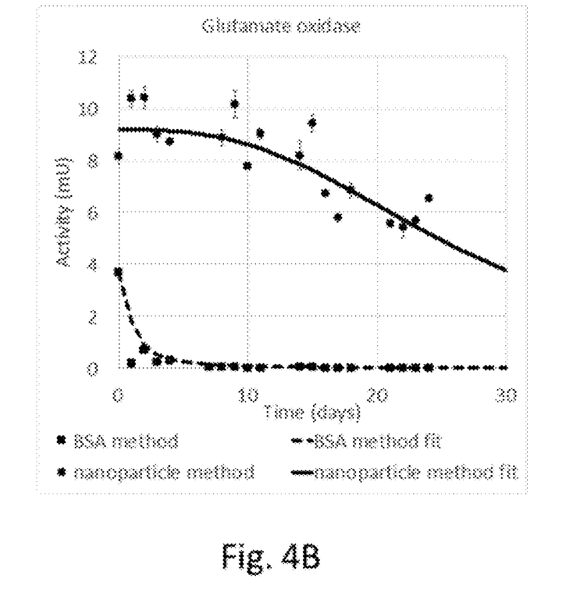
Figure 4C:
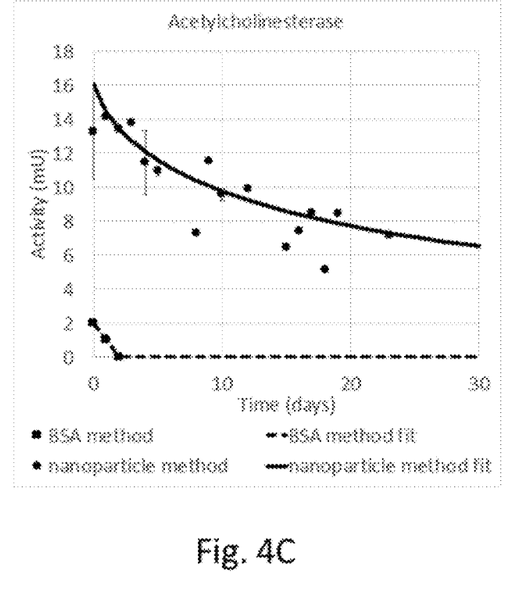

Each enzyme in FIGS. 4A-4C were either exposed to the field standard BSA-glutaraldehyde treatment (square data points, broken lines) or conjugated to the nanoparticle compositions for stabilization (circle data points, solid line). The nanoparticle compositions extend the half-lives of the three enzymes tested—glucose oxidase, glutamate oxidase, and acetylcholinesterase—by at least 3-fold (FIGS. 4A-4C respectively).

VI. Definitions

For convenience, certain terms employed in the specification and appended claims are collected here. These definitions should be read in light of the entire disclosure and understood as by a person of skill in the art.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

The phrase "or," as used herein in the specification and in the claims, should be understood to mean "either or both" of the elements so conjoined, i.e., elements that are conjunctively present in some cases and disjunctively present in other cases. Multiple elements listed with "or" should be construed in the same fashion, i.e., "one or more" of the elements so conjoined. Other elements may optionally be present other than the elements specifically identified by the "or" clause, whether related or unrelated to those elements specifically identified. Thus, as a non-limiting example, a reference to "A or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally eluding more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A nanoparticle composition, comprising: a plurality of nanoparticles, each nanoparticle comprising a base component that comprises a polymer from a non-animal source that mimics a macromolecule of an animal extracellular matrix, wherein a plurality of the polymer molecules are covalently bonded through an internal crosslinking subcomponent to form the structure of each nanoparticle, wherein the internal crosslinking subcomponent has a linkage type selected from the group consisting of amine-acrylamide, amine-vinyl, amine-acrylate, vinyl-hydrazide, and acrylate-hydrazide and wherein the internal crosslinking subcomponent has a molecular weight of less than 10 kDa; and an external binding subcomponent covalently bonded to the base component and configured to bond with and stabilize a bioactive molecule at a dissociation constant of less than 10 micromolar, wherein the bioactive molecule is an animal growth factors.

2. The nanoparticle composition as in claim 1, wherein the base component comprises a carbohydrate mimetic.

3. A nanoparticle composition as claim 2, wherein the carbohydrate mimetic comprises subunits comprising glucose, chitin, alginate, hyaluronic acid, cellulose, sucrose, trehalose, or sucralose.

4. The nanoparticle composition as in claim 1, wherein the external binding subcomponent comprises a sulfate group configured to bond with an amine group of the bioactive molecule.

5. The nanoparticle composition as in claim 1, wherein the average diameter of the particles is less than 200 nm.

6. The nanoparticle composition as in claim 1, wherein the bioactive molecule is comprised in the nanoparticle with a density of at least 0.1 ug of bound bioactive molecule per mg of nanoparticle.

7. The nanoparticle composition as in claim 1, wherein the bioactive molecule is selected from EGF, VEGF, TGF, NGF, growth factors from an activated stem cell culture, and combinations of these.

8. A nanoparticle composition as in claim 1, wherein the bioactive molecule binds the nanoparticle with a dissociation constant less than 1 micromolar.

9. The nanoparticle composition as in claim 1, wherein the internal crosslinking subcomponent includes an acrylamide or an acrylate type of linkage.

10. A biosensor comprising an electrosensitive surface and the nanoparticle composition of claim 1 deposited thereon.

11. A method for making a nanoparticle composition, comprising: forming a precursor solution, the precursor solution comprising an inverse emulsion which comprises a base component, an external binding component, and an internal crosslinking subcomponent which has a linkage type selected from the group consisting of amine-acrylamide, amine-vinyl, amine-acrylate, vinyl-hydrazide, and acrylate-hydrazide and wherein the internal crosslinking subcomponent has a molecular weight of less than 10 kDa, wherein at least a portion of the base component mimics a macromolecule of the extracellular matrix of an animal; and forming the nanoparticles of claim 1 from the inverse emulsion.

12. The method of claim 11, wherein the bioactive molecule is comprised in the precursor solution in a concentration selected to produce a nanoparticle composition with at least 0.1 µg of bound bioactive molecule per mg of nanoparticle.

13. The method of claim 11, wherein the nanoparticles are removed from the inverse emulsion thereby purifying the nanoparticles.

14. The method of claim 11, further comprising sonicating the precursor solution to form the inverse emulsion.

15. The method of claim 11, wherein a polymer of the base component comprises subunits comprising glucose, chitin, alginate, hyaluronic acid, cellulose, sucrose, trehalose, or sucralose.

* * * * *